United States Patent [19]
Collins et al.

[11] Patent Number: 5,514,689
[45] Date of Patent: May 7, 1996

[54] CRIBROSTATINS 1 AND 2

[75] Inventors: Jeremiah C. Collins, Harbour Heights, Ireland; George R. Pettit, Paradise Valley, Ariz.

[73] Assignee: Arizona Board of Regents, Tempe, Ariz.

[21] Appl. No.: 742,610

[22] Filed: Aug. 8, 1991

[51] Int. Cl.$^6$ .......... A61K 31/47; C07C 217/22; C07C 217/00

[52] U.S. Cl. .......... 514/309; 514/310; 546/141; 546/143

[58] Field of Search .................. 546/141, 143; 514/309, 310

[56] References Cited

U.S. PATENT DOCUMENTS 4,853,400  8/1989  Parsons et al. .......... 546/141

*Primary Examiner*—Bernard Dentz
*Assistant Examiner*—Raymond Covington
*Attorney, Agent, or Firm*—Richard R. Mybeck

[57] ABSTRACT

The blue marine sponge Cribrochalina sp., collected in the Republic of the Maldives, was found to contain the new cell growth inhibitory isoquinolinequinones designated cribrostatin 1 ($8.8 \times 10^{-6}\%$ yield) and 2 ($3.1 \times 10^{-6}\%$ yield) which are active against the P388 lymphocytic leukemia cell line (PS $ED_{50}$ 1.58 µg/mL, PS $ED_{50}$ 2.73 µg/mL, respectively). Importantly, both cribrostatins 1 and 2 have shown selective activity against all of the nine human melanoma cell lines employed by the U.S. National Cancer Institute. Structural determinations of both substances were accomplished utilizing high field NMR (400 MHz) and mass spectral studies. Confirmation of the cribrostatin 1 structure was achieved by X-ray crystallographic techniques.

11 Claims, No Drawings

CRIBROSTATINS 1 AND 2

The work described herein was funded in part by Grant CA 44344-01A1 and PHS Grants CA-16049-07-12 Army Medical Research and Development Command Under Grant No. DAMD17-89-Z-9021. The United States government may have certain rights to the invention.

INTRODUCTION

The present invention relates the Isolation and structural elucidation of two new isoquinolinequinones herein denominated cribrostatin 1 and cribrostatin 2, which are obtained from Cribrochalina sp. (Niphatidae family, Haplosclerida order Demospongiae class) found off of remote islands in the Republic of the Maldives. Cribrostatin 1 demonstrated cytostatic properties {PS $ED_{50}$ 1.58 µg/ml and US National Cancer Institute human cancer cell lines, especially melanoma) and has the following general structural formula:

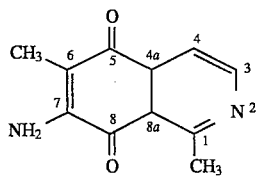

Cribrostatin 2 also demonstrated cytostatic properties (PS $ED_{50}$ 2.73 µg/ml and NCI human cancer cell lines) and has the following general structural formula:

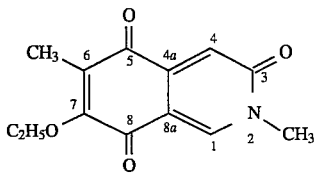

BACKGROUND OF THE INVENTION

In early research devoted to the first systematic investigation of marine animals as new sources of potential anticancer drugs the phylum Porifera rapidly became of increasing importance. Subsequent detection of antineoplastic activity in some of these sponge species led to the isolation of such cell growth inhibitory compounds, as macrocyclic lactones, pyrroles, peptides, and proteins. Meanwhile the isolation of heterocyclic marine sponge constituents such as pyrroles, imidazoles, oxazoles, indoles, pyridines, quinolizidines, pteridines, acridines, other nitrogen systems and quinones has been rapidly accelerating. So far ten isoquinolinequinones have been isolated from blue species of the sponge genera Reniera and Xestospongia. In 1986 an exploratory survey of marine Porifera off remote islands in the Republic of the Maldives was conducted which located a deep blue colored specimen of Cribrochalina sp. (Haplosclerida order) that afforded an orange ethanol extract. The encrusting sponge was found in areas of strong (and dangerous) currents to –45 m in the South side of East reef passages and yielded and ethanol extract that provided 40% life extension (at mg/kg) against the U.S. National Cancer Institute's in vivo murine P388 lymphocytic leukemia (PS system). Bioassay directed isolation using the in vitro PS leukemia led to the discovery of new cytostatic isoquinolinequinones designated cribrostatin 1 and cribrostatin 2.

BRIEF SUMMARY OF THE INVENTION

The present invention relates the isolation and structural elucidation of two new isoquinolinequinones herein denominated cribrostatin 1 and cribrostatin 2, which are obtained from Cribrochalina sp. (Haplosclerida order) found off of remote islands in the Republic of the Maldives. Cribrostatin 1 demonstrated cytostatic properties (PS $ED_{50}$ 1.58 µg/ml and a series of NCI human cell lines) and has the following general structural formula:

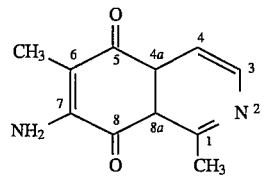

Cribrostatin 2 also demonstrated cytostatic properties (PS $ED_{50}$ 2.73 µg/ml and against certain human cancer cell lines) and has the following general structural formula:

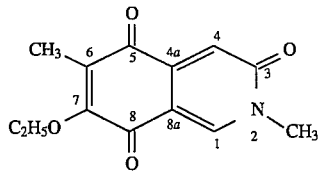

A principal object of the present invention is to isolate and identify new natural substances which can be utilized in the treatment and management of those neoplastic diseases which are characterized by an uncontrolled cell growth and have an established correlation to the NCI protocol for P388 murine lymphocytic leukemia and human cancer cell lines.

Another object of the present invention is to elucidate unequivocally the structure of a newly discovered isoquinolinequinone denominated "cribrostatin 1" so as to provide a readily discernible target for the direction of further synthetic endeavors.

Another object of the present invention is to elucidate unequivocally the structure of a newly discovered isoquinolinequinone denominated "cribrostatin 2" so as to provide a readily discernible target for the direction of further synthetic endeavors.

These and still further objects as shall hereinafter appear are readily fulfilled by the present invention in a remarkably unexpected manner as will be readily discerned from the following detailed description of an exemplary embodiment thereof.

DESCRIPTION OF PREFERRED EMBODIMENT

A 1989 recollection (about 350 kg wet weight) of the Maldive Cribrochalina sp. was subjected to successive ethanol and 1:1 methanol-methylene chloride extractions, and an array of solvent partition separations to provide a PS active methylene chloride extract, which upon evaporation yielded a black semisolid (PS $ED_{50}$ 6.7 µg/mL). The PS active fraction was further separated by a series of size exclusion and partition chromatographic steps utilizing SEPHADEX LH-20 (Scheme I) to afford the new isoquinolinequinones, cribrostatin 1, as red-orange crystals (31 mg, $8.8 \times 10^{-6}$% yield) and the golden-yellow cribrostatin 2 (2 11 mg $3.1 \times 10^{-6}$% yield). The structure of the cytostatic metabolite cribrostatin 1 was determined by HREIMS, a variety of high filed NMR techniques, and confirmed by single-crystal X-ray diffraction analysis.

Mass spectral (by HREIMS) analysis of cribrostatin 1 revealed the molecular formula $C_{11}H_{10}N_2O_2$. The mass spectral fragmentation pattern of cribrostatin 1 exhibited the loss of HCN (27) and CO (28) indicating the possibility of nitrogen containing quinone. The results of UV/vis (232, 265 and 272 nm) and infrared spectra (1681 and 1635 cm$^{-1}$) suggested a quinone while further infrared absorptions (3405 and 3300 cm$^{-1}$) hinted at the presence of a primary amine. The 400 MHz $^1$H-NMR spectrum (Table 1) of cribrostatin 1 displayed a set of doublets at δ7.86 and 8.83 (J=4.9 Hz). The downfield signal at δ8.83 suggested a proton adjacent to nitrogen in a heteroaromatic system The spectrum also exhibited two methyl group resonances at δ2.01 and 2.98 and a broad two proton singlet at δ5.20. The latter signal disappeared on deuterium exchange, again suggesting a primary amino group. The $^{13}$C-NMR spectrum of cribrostatin 1 revealed two carbonyl carbon signals at δ180.90 and 181.85 suggestive of a quinone. Five other quaternary aromatic carbons were evident as well as two aromatic methene carbons and two methyl carbons. The substitution pattern was established by application of a heteronuclear multiple bond correlation (HMBC) NMR experiment (FIG. 1) in conjunction with a $^1$H—$^{13}$C COSY$^{24}$ (cf. FIG. 1). Most of the two and three bond $^1$H—$^{13}$C coupling signals were evident and supported structure 1 for cribrostatin 1. An X-ray crystallographic analysis was used to confirm the structure of cribrostatin 1.

Scheme 1.
Isolation of Cribrostatins 1 and 2

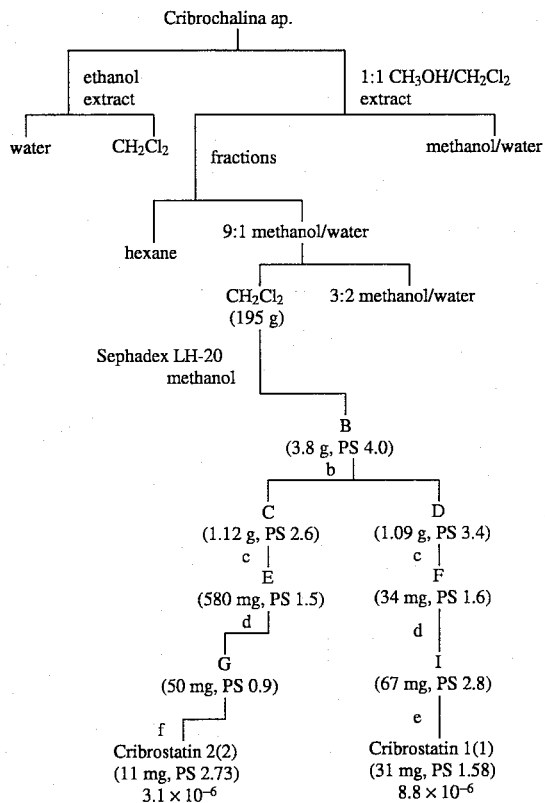

a: PS values are determined in the P388 murine lymphocyctic leukemia cell line and are expressed as the ED$_{50}$ in μg/mL
b: Sephadex LH-20, 3:2 CH$_2$Cl$_2$/methanol
c: Sephadex LH-20, 3:1:1 hexane/toulene/methanol
d: Sephadex LH-20, 8:1:1 hexane/2-propanol/methanol
e: Fractional crystallization
f: Lobar column (silica gel), 10–30% ethyl acetate/CH$_2$Cl$_2$

TABLE 1

The $^1$H and $^{13}$C NMR Spectra of Cribrostatin 1 with Assignments Relative to Tetramethylsilane in Deuteriochloroform.

| Position No. | $^1$H (400 MHz) | $^{13}$C (100 MHz)* |
|---|---|---|
| 1 | | 159.58 |
| 3 | 8.83d, J-4.9Hz | 154.14 |
| 4 | 7.86d. J-4.9Hz | 117.70 |
| 4a | | 140.77 |
| 5 | | 180.90 |
| 6 | | 111.80 |
| 7 | | 146.94 |
| 8 | | 181.85 |
| 8a | | 122.38 |
| 1 - CH$_3$ | 2.98s | 25.69 |
| 6 - CH$_3$ | 2.01s | 9.23 |
| 7 - NH$_2$ | 5.20brs | |

*Two drops of d-6-DMSO were used to aid dissolution

Cribrostatin 2 was isolated employing chromatographic separation on a silica gel LOBAR column with gradient eluent system (1:9–3:7 ethyl acetate in dichloromethane) in the final isolation step. The structure of this quinone (m.p. 194°–195° C., 11 mg) was identified by analyzing the $^{13}$C and $^1$H NMR spectra. The ethoxy group was evident from the presence of a quartet and a triplet at δ4.48 and 1.39 (J=7.0 H$_2$) respectively, with the corresponding carbon signals at δ69.78 and 16.07. The remaining proton and carbon NMR date was very similar to that of mimosamycin except for the distinct lack of any signals due to a methoxy group (Table 2). Further structural support for cribrostatin 2 was obtained from the mass spectral fragmentation pattern. Losses of HCN (27), CH$_3$ (15) and CO (28) were consistent with the structure. A fragmentation ion at 218 was indicative of ethyl group removal from the molecular ion.

TABLE 2

The $^1$H and $^{13}$C NMR Spectra of Cribrostatin 2 with. Assignments Relative to Tetramethylsilane in Deuteriochloroform.

| Position No. | $^1$H (400 MHz) 2 | $^{13}$C (100 MHz 2 |
|---|---|---|
| 1 | 8.25 | 142.02 |
| 3 | | 162.79 |
| 4 | 7.10 | 116.67 |
| 4a | | 138.95 |
| 5 | | 183.52 |
| 6 | | 133.71 |
| 7 | | 159.14 |
| 8 | | 177.37 |
| 8a | | 111.29 |
| 2 - CH$_3$ | 3.66 | 38.37 |
| 6 - CH$_3$ | 2.07 | 9.66 |
| 7 - OCH$_3$ | | |
| 7 - OCH$_2$CH$_3$ | 1.39t, J-7.0Hz 4.48q, J-7.0Hz | 16.07 |

Presently the Cribrochalina sp. constituents are undergoing detailed antineoplastic evaluation. Initial investigation of cribrostatin 1 in the U.S. National Cancer Institute's new in vitro disease-oriented antitumor screen revealed melanoma cell line subpanel specificity is described below. (See: Boyd, status of the NCI preclinical antitumor drug discovery screen: implications for selection of new agents for clinical trial. In: DeVita et al., *Principles and Practices of Oncology, update series,* Vol. 3, No. 10, Lippincott, Philadelphia 1989, pp1–12; and Boyd et al., Data display and analysis strategies from NCI disease oriented in vitro antitumor drug screen. In: Valeriote et al., *Antitumor Drug Discovery and Development,* Kluwer Academic Press, Amsterdam, 1990.) The human tumor cell line panel currently used for these studies consists of a diverse array of 60 different cell lines representing eight major cancer subtypes. All nine of the melanoma cancer line (LOX-1MCI; MALME-3M; M14; M19-MEL; SK-MEL-2; KS-MEL-28; SK-MEL-5; UACC_257; UACC-62) currently included in the panel showed sensitivity greater than the panel mean; $LC_{50}$ values range between $10^{-5}$–$10^{-6}$ molar, with the greatest sensitivity shown by the M19-MEL and the SK-MEL-5 lines.

General Methods

Solvents used for chromatographic procedures were redistilled. The SEPHADEX LH-20 (25–100 μm) employed for gel permeation and partition chromatography was obtained from Pharmacia Fine Chemicals AB, Upsala, Sweden. GILSON FC-220 and FC-202 fraction collectors connected to GILSON HM UV-VIS Holochrome detectors were used for chromatographic fractionation experiments. High speed countercurrent distribution (HSCCD) was utilized employing an ITO multi-layer coil separator-extractor (from P.C. Inc., Potomac, Md.). Silica gel GF Uniplates for TLC were from Analtech, Inc, (Newark, Del.) and Silica GEL Si 60 LOBAR columns from EM Science (Gibbstown, N.J.) were used from chromatographic separation. All TLC plates were viewed with UV light and (or) developed with a ceric sulfate—sulfuric acid spray (heating to approximately 150° C. for 10 min).

The uncorrected melting points were observed with a REICHERT Type 7905 melting point apparatus. The UV-VIS spectra were recorded using a HEWLETT-PACKARD 8450A- UV-VIS spectrophotometer equipped with a HP7225A plotter. IR spectral data were obtained using a NICOLET MX-1 FTIR spectrophotometer. Mass spectra were obtained using a KRATOS MS-50 spectrometer (70ev). The NMR experiments were conducted with BRUKER WH-400 and VARIAN VXR-500 instruments using deuteriochloroform as solvent (TMS internal standard). The x-ray crystallographic experiments were conducted with an ENRAF-NONIUS CAD-4 diffractometer. Data reduction was performed on a Digital Equipment Corporation. MICROVAX Series II computer. Elemental analyses were performed by Spang Microanalytical Laboratories.

To further assist in the understanding of the present invention and not by way of limitation, the following examples are presented.

EXAMPLE 1

Some 350 kg (wet wt) of Cribrochalina sp. was collected at various locations on North and South Male' Atolls (on the south side of east coast passes), Republic of the Maldives, at depths of −5 to −45 m feet and preserved in ethanol. The ethanol solution was decanted and the sponge re-extracted twice with 1:1 methanol-methylene chloride for 5–19 days. The ethanol solution was partitioned with methylene chloride in a counter-current manner, with each portion being partitioned five times. The methylene chloride was removed (evaporation in vacuo) to provide a 1.3 kg residue. (PS $ED_{50}$ 1.25 μg/mL). The chlorocarbon residue was partitioned between hexane and 9:1 methanol-water, the methanol-water phase was diluted to 3:2 methanol-water and partitioned against methylene chloride (the active fraction 127 g, PS $ED_{50}$ 2.6 μg/mL). Meanwhile the two methanol-methylene chloride extracts of the sponge were processed by adding water (15%) to separate a methylene chloride phase, which was evaporated (in vacuo) to dryness (521 g, 323 g; PS $ED_{50}$ 12.5, 0.2 μg/mL). These fractions were combined and partitioned as just summarized for the ethanol extract, yielding an additional active methylene chloride fraction (68 g, PS $ED_{50}$ 6.7 μg/mL).

EXAMPLE 2

A 195 g sample of the PS active methylene chloride fraction from Example 1 was chromatographed on a column of SEPHADEX LH-20 (15×150 cm) in methanol, employing the same solvent as eluant. Twelve distinct fractions were separated, two fractions were combined and designated B (elution volume 3.0 L, 3.8 g, PS $ED_{50}$ 4.0 μg/mL). Fraction B was separated by partition chromatography on a SEPHADEX LH-20 column (5×105 cm) with 3:2 methylene chloride—methanol as eluent to furnish active fraction D (elution volume 300 mL, 1.091 g, PS $ED_{50}$ 3.4 μg/mL). Further partition chromatography on SEPHADEX LH-20 (3×90 cm column) and elution with 3:1:1 hexane—toluene—methanol gave active fraction F (elution 300 mL, 634 mg, PS $ED_{50}$ 1.6 μg/mL). Final partition chromatography on a SEPHADEX LH-20 column (3×90 cm) employing 8:1:1 hexane—2—propanol—methanol as eluent resulted in six distinct composite fractions, of which the fraction labeled I (67 mg, PS $ED_{50}$ 2.8 μg/mL) at elution volume 100 mL, gave on fractional recrystallisation from methylene chloride—methanol cribrostatin 1 as red—orange crystals (31 mg, $8.8 \times 10^{-6}$% yield): mp 220°–235° C. (decomp.); TLC (on silica gel) Rf 0.48 (20:1 methylene chloride—methanol); HREIMS (m/z) 202.0737 ($M^+$ calcd for $C_{11}H_{10}N_2O_2$ 202.0742); UV/vis ($CH_3OH$) $\lambda_{max}$ 207 (ε 8730), 232(4700), 265(4170), 272(4160), 324(537) nm; IR $\lambda_{max}$ (NaCl) 3405, 3300, 1681, 1635, 1602, 1558 $cm^{-1}$; and $^1H$ NMR and $^{13}C$ NMR (see Table 1). Anal. Calcd for $C_{11}H_{10}N_2O_2$: C, 65.33; H. 4.98; N 13.77. Found C, 65.09; H, 5.22; N, 13.77.

EXAMPLE 3

Dark red crystals of cribrostatin 1 from Example 2 separated from a deuteriochloroform—dimethylsulfoxide solution (in an NMR tube) of the quinone upon standing. A crystal of dimension≈0.04×0.40×0.18 mm was obtained by cleavage from a larger crystal. Data were collected (Enraf-Nonius CAD-4 diffractometer) to a maximum of 2θ=140° at 26±1° C. A quadrant of data was collected for the orthorhombic crystal, space group $Pna2_1$, with a=16.792(3), b=14.124(1), c=3.912(1) Å α=β=γ=90°, V=927.8 $Å^3$, $\rho_o$=1.431 g $cm^{-3}$, $\rho_o$–1.447 g $cm^{-3}$ for Z=4. The ω/2θ scan technique was used with graphite monochromated Cu Kα radiation (λ1.54178Å). After Lorentz and polarization corrections, merging of equivalent reflections and rejection of systematic absences, a total of 720 reflections (I>3σ(I)) were used in the structure determination. No absorption correction was made. Direct methods were used in the structure determination. All nonhydrogen atom coordinates were revealed in the initial run of SHELXS-86. Refinement was performed with MOLEN. A Non-Poisson contribution weighing scheme (scheme number 1 in MOLEN) was used with Dunitz-Seller modified weight. The hydrogen atom coordinates were calculated at optimum positions and were included in subsequent final stage of refinement, but were restrained to ride on the atom to which they were bonded. Full matrix least-squares anisotropic refinement on all non-hydrogen atoms, and isotropic temperature factors for hydrogens yielded standard crystallographic residuals of R=0.084, Rw=0.051. A computer generated perspective view of cribrostatin 1, showing 50% probability ellipsoids, is shown below.

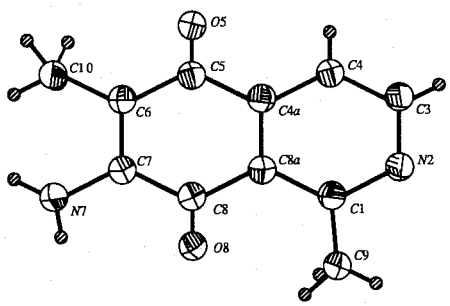

EXAMPLE 4

Separation of the active methylene chloride extract (195 g) from Example 1 on a SEPHADEX LH-20 column (15× 150 cm) in methanol yielded twelve fractions of which the fraction designated B was further separated on a SEPHADEX LH-20 column (5×105 cm) in 3:2 methylene chloride—methanol to yield active fraction C (elution volume 300 mL, 1.12 g, PS $ED_{50}$ 2.6 µg.mL). Additional chromatographic separations on SEPHADEX LH-20 employing the partition solvents recorded in Scheme 1 resulted in active fraction G (50 mg, PS $ED_{50}$ 0.9 µg/mL). Final separation was performed on a LOBAR column (silica gel) employing a gradient eluent (1.9→3.7 ethyl acetate:methylene chloride) with a flow rate of 1.5 mL/min to furnish the title compound as a golden-yellow solid (11 mg, $3.1\times10^{-6}$% yield): mp 194°–195° C. TLC (on silica gel) Rf 0.58 (20:1 methylene chloride-methanol); EIMS m/z 247, 232, 218, 203, 191, 175, 163, 148, 135; UV/vis ($CH_3OH$) $\lambda_{max}$ 209 (ε5829), 328 (4126) nm; IR $\upsilon_{max}$ (KBr) 2953, 2854, 1682, 1643, 1608, 1548 cm$^{-1}$; and $^1H$ NMR and $^{11}C$ NMR (see Table 2) supra.

EXAMPLE 5

Cribrostatin 1 was subjected to the NCI panel cell line and provided especially favorable results for non-small lung cancer (A549/ATCC, HOP-18, and NCI-H460), colon cancer (CoLo 205), and melanoma (MALME-3M, M14, M19-MEL, SK-MEL-2, SK-MEL-28, UACC-257, and UACC-62).

From the foregoing, it is readily apparent that a useful embodiment of the present invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. An isoquinolinequinone denominated herein as Cribrostatin 1 and having the structural formula;

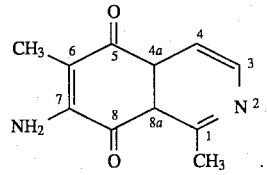

2. An isoquinolinequinone denominated herein as Cribrostatin 2 and having the structural formula;

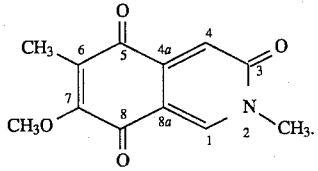

3. A composition of matter according to claim 1 wherein said cribrostatin 1 is extracted from Cribrochalina sp. (Haplosclerida order).

4. A composition of matter according to claim 3 wherein said cribrostatin 1 is purified.

5. A composition of matter according to claim 3 wherein said cribrostatin 1 is more concentrated by a factor of at least $10^6$ than can be found naturally occurring in said Cribrochalina sp.

6. A composition of matter according to claim 4 wherein said cribrostatin 1 is more concentrated by a factor of at least $10^6$ than can be found naturally occurring in said Cribrochalina sp.

7. A composition of matter according to claim 2 wherein said cribrostatin 2 was extracted from Cribrochalina sp. (Haplosclerida order).

8. A composition of matter according to claim 7 wherein said cribrostatin 2 is purified.

9. A composition of matter according to claim 7 wherein said cribrostatin 2 is more concentrated by a factor of at least $10^6$ than can be found naturally occurring in said Cribrochalina sp.

10. A composition of matter according to claim 8 wherein said cribrostatin 2 is more concentrated by a factor of at least $10^6$ than can be found naturally occurring in said Cribrochalina sp.

11. A method for treating human cells which comprises administering a pharmaceutically acceptable carrier combined with an amount of an active agent selected from the group comprised of cribrostatin 1 and cribrostatin 2, effective to inhibit the growth and effects of tumors in human cells to which the administration is effected.

* * * * *